(12) United States Patent
McIntyre

(10) Patent No.: US 7,404,800 B2
(45) Date of Patent: Jul. 29, 2008

(54) HYBRID LVEDP MONITOR

(76) Inventor: Kevin M. McIntyre, 160 Commonwealth Ave., Suite 801, Boston, MA (US) 02116

( * ) Notice: Subject to any disclaimer, the term of this patent is extended or adjusted under 35 U.S.C. 154(b) by 411 days.

(21) Appl. No.: 11/105,306

(22) Filed: Apr. 13, 2005

(65) Prior Publication Data

US 2006/0235309 A1 Oct. 19, 2006

(51) Int. Cl.
*A61B 5/02* (2006.01)
(52) U.S. Cl. ........................ 600/485; 600/486
(58) Field of Classification Search ............... 600/485, 600/486
See application file for complete search history.

(56) References Cited

U.S. PATENT DOCUMENTS

| | | | |
|---|---|---|---|
| 4,869,261 | A | 9/1989 | Penáz |
| 5,291,895 | A | 3/1994 | McIntyre |
| 6,511,436 | B1 | 1/2003 | Asmar |
| 6,580,946 | B2 | 6/2003 | Struble |
| 6,610,018 | B1 * | 8/2003 | McIntyre ............... 600/485 |
| 6,832,113 | B2 | 12/2004 | Belalcazar |
| 2003/0083582 | A1 | 5/2003 | Hirsch |
| 2003/0097158 | A1 * | 5/2003 | Belalcazar ............... 607/32 |
| 2003/0130581 | A1 | 7/2003 | Salo et al. |
| 2004/0106874 | A1 * | 6/2004 | Eigler et al. ............... 600/486 |

OTHER PUBLICATIONS

Prunier F et al., "Doppler echocardiographic estimation of left ventricular end-diastolic pressure after MI in rats;" Am J Physiol Heart Circ Physiol 283: H346-H352, 2002.*

Firstenberg MS et al., "Relationship of Echocardiographic Indices to Pulmonary Capillary Wedge Pressures in Healthy Volunteers," J Am Coll Cardiol 36: 1664-1669, 2000.*

Schwammenthal E et al., "Noninvasive Assessment of Left Ventricular End-Diastolic Pressure by the Response of the Transmitral A-Wave Velocity to a Standardized Valsalva Maneuver," Am J Cardiol 86:169-174, 2000.*

Ommen SR et al., "Clinical Utility of Doppler Echocardiography and Tissue Doppler Imaging in the Estimation of Left Ventricular Filling Pressures: A Comparative Simultaneous Doppler-Catheterization Study," Circulation 102: 1788-1794, 2000.*

Brunner-LaRocca HP et al., "Left ventricular end-diastolic pressure can be estimated by either changes in transmitral inflow pattern during valsalva maneuver or analysis of pulmonary venous flow," J Am Soc Echocardiogr 13(6): 599-607, 2000.*

Channer KS et al., "Estimation of left ventricular end-diastolic pressure by pulsed Doppler ultrasound," Lancet 1(8488): 1005-1007, 1986 (abstract).*

Mulvagh S et al., "Estimation of left ventricular end-diastolic pressure from Doppler transmitral flow velocity in cardiac patients independent of systolic performance," J Am Coll Cardiol 20: 112-119, 1992 (abstract).*

(Continued)

*Primary Examiner*—Robert L. Nasser, Jr.
*Assistant Examiner*—Karen E Toth
(74) *Attorney, Agent, or Firm*—Fish & Richardson P.C.

(57) ABSTRACT

An apparatus for validating a non-invasively obtained estimate of LVEDP includes a non-invasive system for non-invasively obtaining a first estimate of the LVEDP; an invasive system for invasively obtaining a second estimate of the LVEDP concurrent with the first estimate; and a processor for comparing the first and second estimates of the LVEDP.

18 Claims, 3 Drawing Sheets

OTHER PUBLICATIONS

Weilenmann D et al., "Noninvasive Evaluation of Pulmonary Capillary Wedge Pressure by BP Response to the Valsalva Maneuver," Chest 122: 140-145, 2002.*

A.M.M. Van Der Kraaij et al., "Noninvasive estimation of the pulmonary-capillary wedge pressure," *The Thoraxcentre Journal*, 1994, 3 pages.

* cited by examiner

HYBRID LVEDP MONITOR

FIELD OF INVENTION

This invention relates to medical diagnostic devices, and in particular, to devices for measurement of pressure within the heart.

BACKGROUND

In the diagnosis of many conditions, for example heart disease, it is useful to recognize perturbations in intravascular fluid volume. For example, an increase in intravascular volume may indicate decompensated heart failure. A decrease in intravascular volume can indicate dehydration. Both of these conditions are potentially dangerous. In some cases, these conditions are life-threatening.

An important parameter for the recognition and quantification of such perturbations is the left-ventricular filling pressure. This pressure is best quantified by measurement of left-ventricular end-diastolic pressure, "LVEDP."

A particularly accurate way to measure the LVEDP is to catheterize the left ventricle of the heart. This provides a direct measurement of the LVEDP. Because of its accuracy, this method is often said to provide the "gold standard" for LVEDP measurement.

However, catheterizing the left ventricle is highly invasive and dangerous, with complications that include stroke and death. Consequently, it is undesirable as a routine diagnostic test. Because of the danger inherent in catheterizing the left ventricle, a direct measurement of LVEDP is generally available only when a catheter has been placed in a patient's aorta for some other reason, for example during diagnostic coronary angiography to document the presence and severity of coronary artery disease. In this setting, LVEDP is measured by moving the coronary angiography catheter tip below the coronary artery and across the aortic valve so that the tip of the catheter is in the patient's left ventricle. Once the catheter tip is in the left ventricle, LVEDP can be measured directly.

A more common approach is to indirectly measure LVEDP. This is done by passing a pulmonary-artery catheter through the right ventricle of the heart and into the lungs, where it is positioned to measure the pressure in the capillary bed of the lungs. This pressure, which is referred to as the "pulmonary capillary wedge pressure" (PCWP), provides a clinically useful estimate of the filling pressure of the left ventricle of the heart. While the insertion of a pulmonary artery catheter comes with its own set of complications, it is much less dangerous than catheterizing the left ventricle of the heart.

SUMMARY

In one aspect, the invention is an apparatus for validating a non-invasively obtained estimate of LVEDP. Such an apparatus includes a processor, a non-invasive system for non-invasively obtaining a non-invasive estimate of the LVEDP and an invasive system for invasively obtaining an invasive estimate of the LVEDP concurrent with the non-invasive estimate. The processor compares the invasive and non-invasive estimates of the LVEDP.

In some embodiments, the invasive system includes a catheter having a pressure sensor mounted at a distal tip thereof. Exemplary catheters include a pulmonary catheter and a left-ventricular catheter.

In other embodiments, the invasive system is configured to generate the invasive estimate on the basis of a measured PCWP.

In yet other embodiments, the processor is configured to generate calibration data to be applied to the non-invasive estimate to cause the non-invasive estimate to conform to the invasive estimate.

Exemplary non-invasive systems include systems for non-invasively constructing a left-ventricular pressure waveform.

Other exemplary non-invasive systems include those having first and second amplitude sensors for non-invasively obtaining corresponding first and second pressure waveforms, an event sensor for detecting a time of occurrence of an event in a cardiac cycle, and a processor in communication with both the first and second amplitude sensors and with the event sensor. The processor is configured to select a segment from each of first and second waveforms and to connect those selected segments on the basis of the time of occurrence of the event.

In another aspect, the invention includes a method for validating a non-invasively obtained estimate of LVEDP. The method includes non-invasively obtaining a non-invasive estimate of an LVEDP, invasively obtaining an invasive estimate of the LVEDP, and comparing the non-invasive and invasive estimates of the LVEDP.

In some practices, obtaining an invasive estimate includes positioning a pulmonary catheter to measure a PCWP, and optionally generating the invasive estimate on the basis of the measured PCWP.

Other practices include generating calibration data on the basis of the non-invasive and invasive estimates, and applying the calibration data to the non-invasive estimate to cause the non-invasive estimate to conform to the invasive estimate.

In alternative practices, obtaining the first estimate includes non-invasively constructing a left-ventricular pressure waveform.

Another aspect of the invention features an apparatus for validating a non-invasively obtained estimate of LVEDP. Such an apparatus includes non-invasive means for obtaining a first estimate of the LVEDP, invasive means for invasively obtaining a second estimate of the LVEDP concurrent with the first estimate, and means for validating the first estimate at least in part on the basis of the second estimate.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
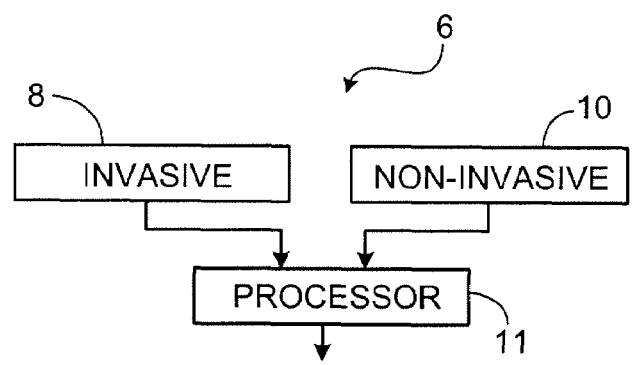
FIG. 1 shows a hybrid LVEDP monitor.

A hybrid LVEDP monitor 6, shown in FIG. 1, includes an invasive system 8, for invasively determining LVEDP, either directly or indirectly, and a non-invasive system 10, for non-invasively determining LVEDP. Both the invasive system 8 and the non-invasive system 10 generate output pressure signals independently of each other. These output pressure signals are provided to a processor 11 that compares the output pressure signals and derives therefrom an error signal.

In most cases, only the non-invasive system 10 is used to monitor the LVEDP.

The invasive system 8 is used occasionally to confirm the correct functioning of the non-invasive system 10 or to provide data for use in calibrating the non-invasive system 10. The error signal generated by the processor 11 provides a way to validate the accuracy of the non-invasive system 10 and/or to indicate any "error" in the measurement provided by the invasive system 8. For example, in a cardiac catheterization lab, one can obtain a measurement from an invasive system 8 simultaneously with measurements made by the non-invasive system 10. Examples of invasive systems 8 include PA catheters, for estimating LVEDP using pulmonary capillary wedge pressure, and LV catheters, for directly measuring LVEDP. In many cases, the non-invasive system 8 provides more accurate estimates of LVEDP than those obtained from a pulmonary artery catheter. This is because the non-invasive system 8 can be calibrated using simultaneous measurements made by a catheter tip inserted directly into the left ventricle.

Another purpose of the invasive system 8 is to provide data useful for calibrating the non-invasive system 10. In this case, the invasive system 8 and the non-invasive system both estimate the LVEDP. The measurements obtained by the non-invasive system 10 are then correlated with corresponding measurements obtained with the invasive system 8. Calibration coefficients used to correlate the invasive system measurements and the non-invasive system measurements are then used for future monitoring of the LVEDP using only the non-invasive system 10.

A typical non-invasive system 10 is one that synthesizes a left-ventricular pressure waveform over a complete cardiac cycle by piecing together segments of the left-ventricular pressure waveform, each of which provides the left-ventricular pressure waveform over a limited portion of the cardiac cycle. The constituent segments of the desired waveform, the data needed to shift those segments in time, and the data needed to calibrate the constituent segments are obtained from a collection of non-invasive diagnostic devices. One example of a non-invasive system is that described in U.S. Pat. No. 6,610,018, the contents of which are incorporated herein by reference.

Figure 2:
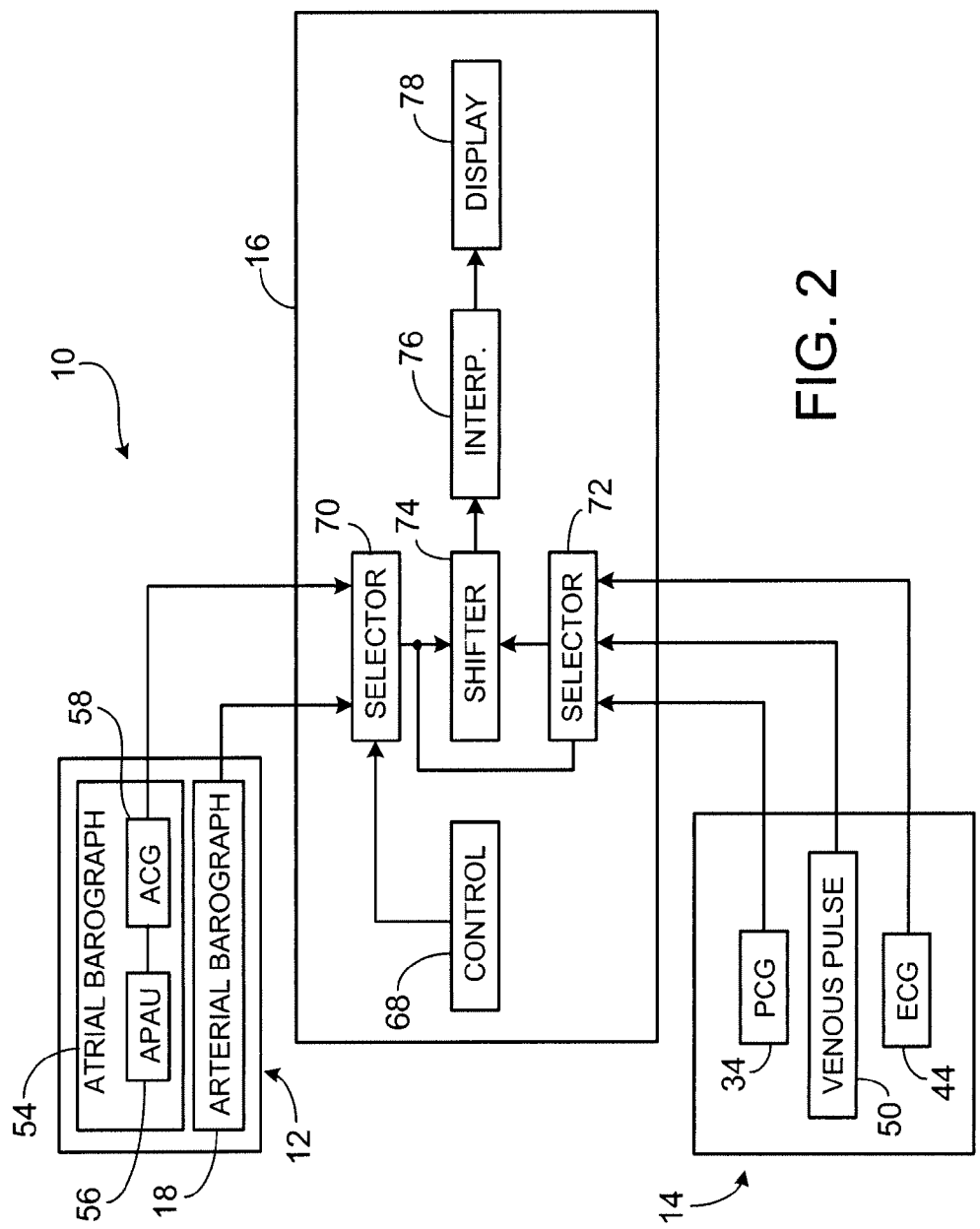
FIG. 2 shows a non-invasive system.

FIG. 2 shows a non-invasive system 10 having two groups of diagnostic devices. A first group 12 includes non-invasive pressure measurement devices that provide signals indicative of a pressure waveform existing in a portion of the cardiovascular system. Such devices are collectively referred to herein as "barographs;" the pressure waveforms that they produce are collectively referred to as "barograms." A second group 14 includes non-invasive diagnostic devices that detect the occurrence of particular events during the cardiac cycle. These devices are collectively referred to as "event detectors." It will be appreciated that, in addition to providing data indicative of pressure, the output of one or more non-invasive pressure measurement devices from the first group 12 can also provide data indicative of the occurrence of particular events during the cardiac cycle.

The barograms and the outputs of the event detectors are provided to a software system 16 whose function is to select portions of the barograms and to synchronize those portions to form one continuous curve representative of the left-ventricular pressure during the entire cardiac cycle. This synthesized curve will be referred to herein as the "LV barogram."

One barograph from the first group 12 can be an arterial barograph 18 in non-invasive communication (i.e. by any non-invasive means) with a patient's arterial system. The arterial barograph 18 generates a waveform (shown in FIG. 3 and hereafter referred to as the "arterial barogram") that shows arterial pressure as a function of time. For that portion of the cardiac cycle during which the aortic valve is closed, the corresponding portion of the arterial barogram is not closely related to the left-ventricular pressure. However, during an ejection phase 28 of the cardiac cycle, the aortic valve is open and the left ventricle and aorta are (absent abnormalities of the aortic valve, or other conditions obstructing flow out of the left ventricle, in fluid communication with each other. Consequently, for those portions of the cardiac cycle, the arterial barogram does correspond to the LV barogram.

Figure 3:
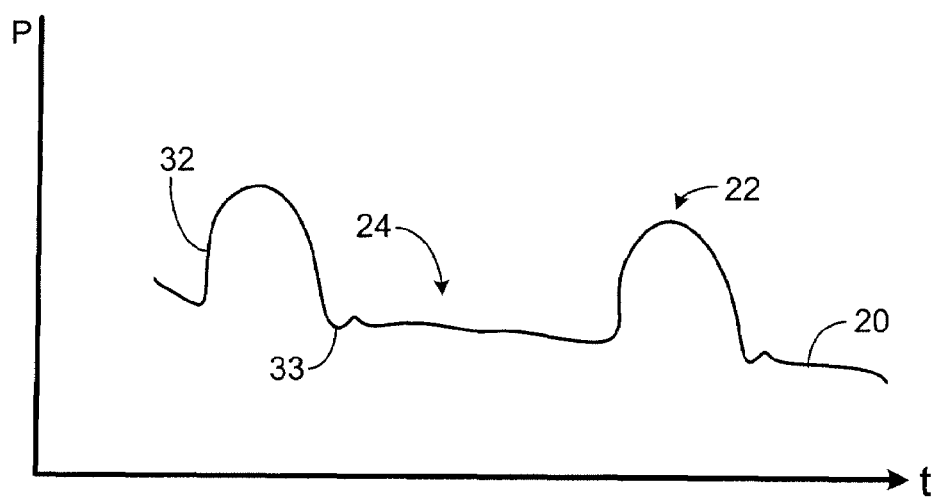
FIG. 3 shows an arterial barogram and an atrial barogram.

As shown in FIG. 3, an arterial barogram 20 thus includes a set of first portions 22 that are identical (absent abnormalities of the aortic valve or other condition obstructing flow out of the left ventricle) to the left-ventricular pressure, and a set of second portions 24 that are irrelevant to the measurement of left-ventricular pressure. Each first portion 22 corresponds to a time interval during which the aortic valve is open. Each second portion 24 corresponds to a time interval during which the aortic valve is closed. To be of use in synthesizing the LV barogram, the arterial barogram 20 must therefore be further processed to discard the second portions 24 and to retain only the first portions 22. This requires the ascertainment of boundaries between the first and second portions 22, 24 of the arterial barogram 20.

Figure 4:
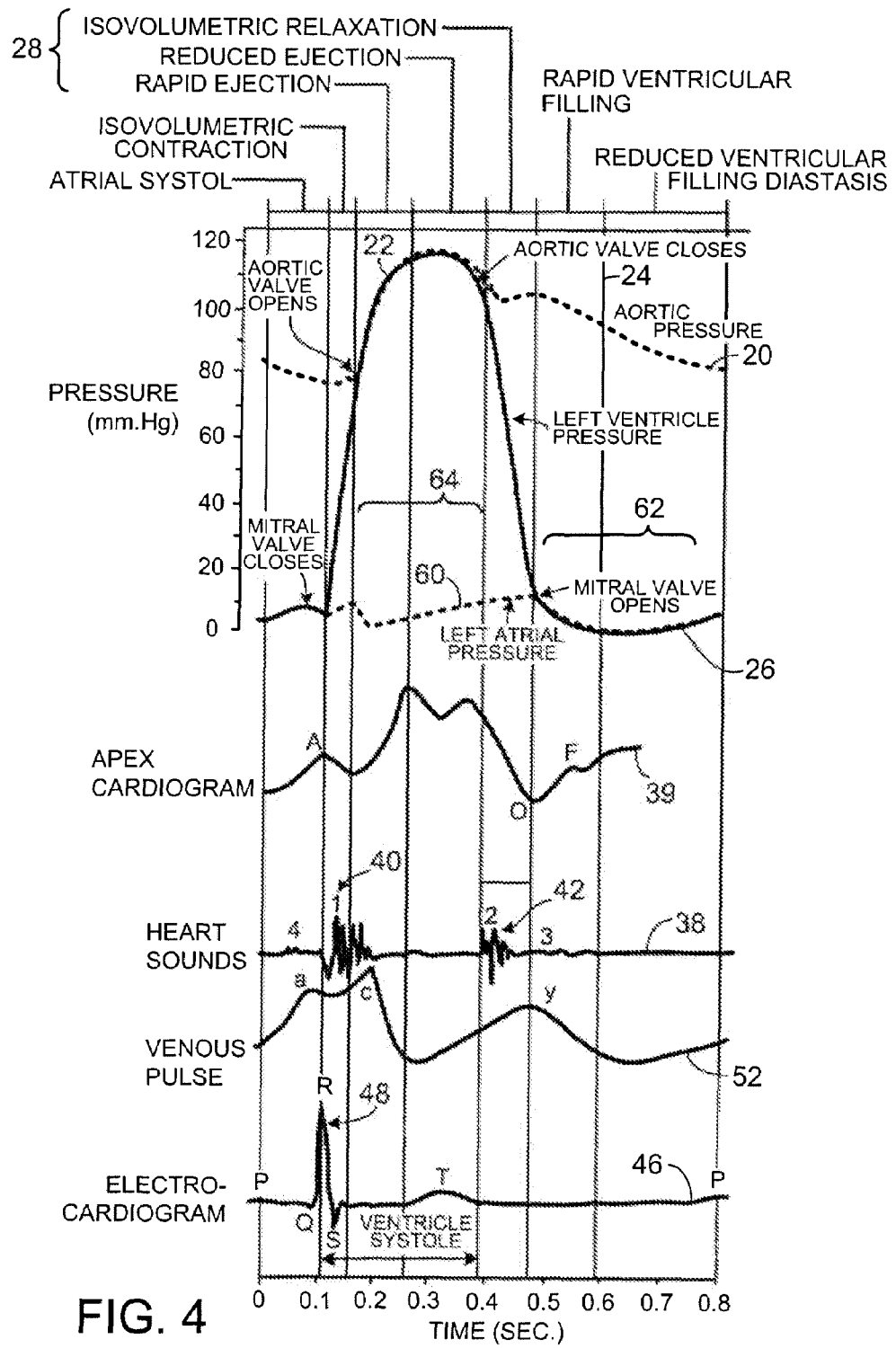
FIG. 4 shows LV pressure during a cardiac cycle.

FIG. 4 shows, for a patient in good cardiovascular health, a typical arterial barogram 20 overlaid on an LV barogram 26 obtained by direct measurement with a catheter in the left ventricle. A typical first portion 22 overlaps the LV barogram 26 during the ejection phase 28 of the cardiac cycle. A typical second portion 24 deviates significantly from the LV barogram 26. A time interval associated with the first portion 22 of an arterial barogram 20 will be referred to as a "pump interval" because during this interval, the left ventricle is pumping blood into the arterial system.

The opening and closing of the aortic valve delineate the extent of the pump interval. For the particular example shown in FIG. 3, the opening and closing of the aortic valve are associated with a sharp rise 32 in pressure and a sharp decline in pressure prior to the occurrence of a dicrotic notch 33 respectively. However, in a patient with poor cardiovascular health, these features may not be as readily apparent. Even in cases where these features are apparent, the instants at which the aortic valve opens and closes are difficult to determine with precision because the elasticity of the arteries, and other mechanical properties of the arterial system, can introduce delays in the response of the arterial pressure to the activity of the aortic valve. To some extent, these delays can be corrected for by correlating them with the occurrence of particular features in an electrocardiogram or phonocardiogram, or by measuring the delays in various population groups and developing relevant correction factors.

Certain events, such as the closing and opening of heart valves, are detected by one or more event detectors from the second group 14 of diagnostic devices shown in FIG. 2. These event detectors determine the instants at which certain key events in the cardiac cycle occur. These instants can then be used to identify boundaries between first and second portions 22, 24 of the arterial barogram 20.

For example, in the illustrated non-invasive system 10, an event detector that includes a phonocardiograph 34 detects the acoustic signal generated by the aortic and mitral valves as they close. FIG. 4 shows, on the same time axis as the LV barogram 26, a representative phonocardiogram 38 provided by the phonocardiograph 34. Alternatively, an echocardiogram can be used to precisely time the opening and closing of the aortic, mitral, tricuspid, and pulmonic valves. As is apparent from FIG. 4, the beginning of a first acoustic pulse 40 marks the closing of the mitral valve. The beginning of a second acoustic pulse 42 marks the closing of the aortic valve. For event detectors that include a jugular venous pulse acquisition unit 50, the "X-descent" of the venous pulse 52 in FIG. 4 marks the opening of the tricuspid valve.

In some embodiments, an atrial barograph 54 can be used to identify the occurrence of particular events in the cardiac cycle. For those embodiments in which the atrial barograph 54 includes an apex cardiograph 58 or a similar device, certain features of the apex cardiogram can be used to identify the occurrence of events in the cardiac cycle. For example, the "O" point, or nadir of the apex cardiogram can be used to mark the opening of the mitral valve. FIG. 4 shows, on the same time axis as the LV barogram 26, a representative apex cardiogram 39 provided by the apex cardiograph 58. In other embodiments, opening of the mitral and/or tricuspid valve is detected by echocardiography.

Alternatively, an event detector can include an electrocardiograph 44. In such a case, the event detector uses selected features of an electrocardiogram to identify the occurrence of selected events. FIG. 4 shows an electrocardiogram 46 on the same time axis as the LV barogram 26. As is apparent from FIG. 4, the "R" spike of the QRS-wave 48 is associated with closing of the mitral valve. The opening of the aortic valve is known to occur after a known interval following the closing of the mitral valve. In addition, the opening of the aortic valve is marked by the up-stroke of the aortic pressure trace. Each of these parameters can also be accurately and reliably identified by echocardiography.

As suggested above, an event detector can also include a venous pulse acquisition unit 50, a representative output of which is shown in FIG. 4 on the same time axis as the LV barogram 26. The output 52 of the venous pulse acquisition unit 50 has a peak associated with the opening of the mitral valve. Since the opening of the mitral valve may not be readily discernible in the phonocardiogram 38, the availability of data from the venous pulse acquisition unit 50 can be useful in fixing the time at which the mitral valve opens. Similarly, an event detector can be an echocardiogram, which detects opening and closing of the mitral valve.

Following closure of the aortic valve, and the end of the pump interval, the left ventricle continues to relax. At some point, marked by the nadir of the apex cardiogram (indicated by "O" in FIG. 4), or by using an appropriate feature identified by an alternative non-invasive technology, such as echocardiography, the pressure within the left ventricle falls to the point at which the mitral valve opens. This begins a fill interval, during which the mitral valve is open, the aortic valve is closed, and oxygenated blood flows into the left ventricle. In the absence of mitral valve disease, the left atrium and the left ventricle are in fluid communication during the fill interval. Hence, absent mitral value disease, the left-ventricular pressure is a function of, or correlated with, the left-atrial pressure. Accordingly, a non-invasive measure of left-atrial pressure during the fill interval can provide information indicative of the atrial barogram.

Referring again to FIG. 2, in one embodiment, the first group 12 of diagnostic devices also includes an atrial barograph 54 in non-invasive communication with the patient's left atrium. The atrial barograph 54 provides a left-atrial pressure waveform, hereafter referred to as the "atrial barogram," that shows the left-atrial pressure as a function of time. The atrial barograph 54 thus provides an indication of ventricular pressure during the fill interval.

One example of an atrial barograph 54 includes an atrial-pressure acquisition-unit 56, such as that described in McIntyre U.S. Pat. No. 5,291,895 issued on Mar. 8, 1994, used in conjunction with an apex cardiograph 58 (or other non-invasive device, such as an echocardiograph unit). An atrial-pressure acquisition-unit 56 of the type disclosed therein provides values of atrial pressure at key points of the cardiac cycle. In particular, the atrial-pressure acquisition-unit 56 provides the LV pre-A EDP (pre-atrial contraction end diastolic pressure) and the LV post-A EDP (post-atrial contraction end diastolic pressure). The apex cardiograph 58 provides an apex cardiogram having the relative shape of the atrial pressure waveform. The absolute values of pressure from the atrial-pressure acquisition-unit 56 can thus be used to calibrate the apex cardiogram. The apex cardiogram and the pressure values provided by the atrial-pressure acquisition-unit 56 can thus be combined to provide the data needed to inscribe an atrial barogram. In addition, an echocardiograph can provide accurate measurements in real time.

Like the arterial barogram 20, the atrial barogram includes a set of first portions that are useful for the measurement of left-ventricular pressure and a set of second portions that are not relevant to the measurement of left-ventricular pressure. Each first portion corresponds to a fill interval during which the mitral valve is open. Each second portion corresponds to a pump interval during which the mitral valve is closed. Like the arterial barogram 20, the atrial barogram must be further processed to separate the first portions from the second portions. As was the case with the arterial barogram 20, this requires ascertainment of the boundaries between first and second sections.

FIG. 4 also shows a representative atrial barogram 60 superimposed on the same time axis as an LV barogram 26 measured directly by a catheter in the left ventricle. As is apparent from FIG. 4, absent mitral valve disease, the atrial barogram 60 tracks the LV barogram 26 closely during the fill interval, but deviates significantly once the mitral valve is closed.

In general, it may not be possible to reliably determine whether the mitral valve is closed by examining features of the atrial barogram 60. Moreover, since disease is detected by an improper response (pressure) to a stimulus (valve activity), it would be illogical to use the response to identify the occurrence of the stimulus. However, the same event detectors that were used to separate first and second portions of the arterial barogram 20 can be used to separate first and second portions of the atrial barogram 60. In addition, echocardiography can be used to detect opening and closing of the mitral valve when necessary.

As discussed above in connection with FIG. 4, the opening of the mitral valve can (in the absence of mitral valve disease) be detected on the basis of the nadir, or "O" point of the apex cardiogram or on the basis of the venous pulse 52. Closure of the mitral valve is associated with both the "R" spike on an electrocardiogram and with an acoustic pulse on the phonocardiogram 38. Alternatively, closure of the mitral valve can also be identified and timed accurately by echocardiography.

The cardiac cycle also includes two, relatively brief intervals during which both the aortic valve and the mitral valve are closed. These intervals, during which isometric contraction takes place, are referred to as the upstroke and downstroke intervals. The upstroke interval begins when, as the left ventricle begins its contraction, the left-ventricular pressure exceeds the left-atrial pressure. This causes the mitral valve to close. The upstroke interval ends when, as the left ventricle continues to contract, the pressure developed within the left ventricle exceeds the pressure in the aorta. This change in the sign of the pressure difference opens the aortic valve, thereby ending the upstroke interval and beginning the pump interval. The downstroke interval begins when, as the left ventricle relaxes, pressure in the aorta exceeds the declining left-ventricular pressure. The resulting pressure differential closes the aortic valve. The downstroke interval continues until the left ventricle relaxes enough to cause the left-ventricular pressure to fall below the left-atrial pressure. This change in the sign of the pressure difference opens the mitral valve, thereby ending the downstroke interval and beginning the fill interval.

During the upstroke and downstroke intervals, the fluid in the left-ventricle is isolated from the remainder of the circulatory system. Hence, it is not currently possible to obtain the shape of the pressure waveform during these relatively brief intervals. However, the upstroke and downstroke intervals are so brief that for all practical purposes, the LV barogram 26 during these intervals can be inscribed by connecting the known pressures at the beginning and end of the interval by a straight line. Alternatively, accurate markers and time corrections can be developed from simultaneous LV catheterizations and non-invasive measurements, thereby providing a correction factor for various population groups.

The derivative of the pressure waveform ("LV dP/dt") during the upstroke interval is a useful quantitative indicator of heart function. This can be predicted with a clinically useful level of accuracy from systemic arterial pressure by measuring dP/dt of the systemic arterial up-stroke (absent aortic valve disease) and applying a suitable correction factor. Under these circumstances, one can empirically correct the pressure waveform during these intervals. Such correction factors may be required because the closure of the aortic valve is detected by measuring a pressure wave at a point far from the heart. As a result, there is a time delay between the closure of the aortic valve and the detection of that closure. This delay causes the measured derivative of the pressure waveform during the upstroke interval to be smaller than it should be. Such correction factors can be empirically determined by comparing LV measurements made directly and indirectly in a large number of patients and using statistics derived from such measurements to correct the measured derivative of the pressure waveform.

In other cases, the arterial barogram 20 can also provide information about additional hemodynamic parameters, such as stroke output and work performed by each stroke. This can be achieved by observing the duration of the pump interval and correlating that duration with stroke volume. A formula relating the duration of the pump stroke output interval (i.e., the "systolic ejection period") with the stroke volume is well-known and well-accepted in the medical literature. Alternatively, both echocardiography and impedance plethysmography can provide accurate measurement of stroke volume.

The area under the first portion 22 of the arterial barogram 20 can also provide information about these additional hemodynamic parameters. This can be achieved by obtaining calibration data using a non-invasive flow measurement technique. Exemplary techniques include non-echo-Doppler non-invasive flow measurement techniques, such as echo cardiography (as described on page 9 of vol. 6, No. 2 of a journal entitled "Congestive Heart Failure" and published in March/April 2000), Doppler measurements (as described in an article by Williams and Labovitz entitled "Doppler Estimation of Cardiac Output: Principles and Pitfalls" and published in Echocardiography 1987, pages 355-374) and non-invasive impedance determination of cardiac output (as described by Hanley and Stamer in "Pressure volume studies in man: an evaluation of the duration of the phases of systole" as published in 1969 in the Journal of Clinical Investigation, vol. 48, pp. 895-905. The calibration data thus obtained is thereafter used to determine the stroke volume from the integral of the arterial barogram 20 over the first portion. To the extent that a patient's systemic arterial pressure remains relatively stable, any changes in the value of that integral will indicate a change in stroke output.

The software system 16 includes a first selection process 70 having inputs connected to barographs in the first group of diagnostic devices. The first selection process 70 has an output that corresponds to the LV barogram 26 during either the fill interval or the pump interval. The particular input to be selected is controlled by a control process 68 on the basis of what portion of the barogram was last inscribed.

Similarly, the software system also includes a second selection process 72 having inputs connected to event detectors in the second group of diagnostic devices. The second selection process 72, like the first, has an output that corresponds to a selected one of its inputs. The particular input to be selected depends on the output of the first selection process 70.

The software system 16 further includes a shift process 74 having a first and second input. The first input of the shift process 74 is connected to the output of the first selection process 70 and the second input of the shift process 74 is connected to the output of the second selection process 72. The output of the shift process 74 is its first input shifted in time by an amount derived from its second input.

The output of the shift process 74 is provided to an interpolation process 76 whose function is to inscribe the upstroke and downstroke intervals on the basis of the temporal endpoints of the pump and fill intervals and the values of the inscribed LV barogram 26 at those endpoints. The interpolation process 76 then provides its output to a display 78, which renders the LV barogram on a CRT, a strip chart, or any similar display.

The invasive system 8 typically includes a catheter 80 having a pressure sensor 82 at a distal tip thereof. The pressure sensor 82 is coupled to a transducer 84 that generates a pressure signal indicative of the PCWP. The catheter 80 is typically inserted into a vein in the arm or in the groin and into the right ventricle. The distal tip is positioned so that the pressure sensor 82 senses the PCWP.

The processor 11 typically executes software for receiving pressure signals from the non-invasive system and the invasive system and deriving from those signals a comparison between a non-invasively obtained PCWP and an invasively obtained PCWP, or alternatively, a comparison between a non-invasively obtained LVEDP and an invasively obtained LVEDP.

In use, both the non-invasive system 10 and the invasive system 8 concurrently monitor LVEDP. Once the non-invasive system 10 has been demonstrated to be as accurate as the invasive system 8 at monitoring LVEDP in the particular patient, the invasive system 8 can be removed or otherwise disabled, and monitoring can be carried out with only the non-invasive system 10. The ability to now monitor the LVEDP non-invasively means that monitoring can be carried out at home, with data being communicated to a central monitoring station via a telephone line of other data communication link.

Having described the invention, and a preferred embodiment thereof, what is claimed as new, and secured by Letters Patent is:

1. An apparatus for validating a non-invasively obtained estimate of LVEDP, the apparatus comprising:
   a non-invasive system for obtaining a non-invasive estimate of the LVEDP;
   an invasive system for obtaining an invasive estimate of the LVEDP concurrent with the non-invasive system; and
   a processor for comparing the non-invasive and invasive estimates of the LVEDP;
   wherein the non-invasive system includes:
   a first amplitude sensor for non-invasively obtaining a first pressure waveform;
   a second amplitude sensor for non-invasively obtaining a second pressure waveform;
   an event sensor for detecting a time of occurrence of an event in a cardiac cycle; and
   a processor in communication with said first and second amplitude sensors and with said event sensor, said processor being configured to select a segment from each of said first and second waveforms and to connect said segments on the basis of said time of occurrence of said event.

2. The apparatus of claim 1, wherein the invasive system comprises a catheter having a pressure sensor mounted at a distal tip thereof.

3. The apparatus of claim 2, wherein the catheter comprises a pulmonary catheter.

4. The apparatus of claim 2, wherein the catheter comprises a left-ventricular catheter.

5. The apparatus of claim 1, wherein the invasive system is configured to generate the invasive estimate on the basis of a measured PCWP.

6. The apparatus of claim 1, wherein the processor is configured to generate calibration data to be applied to the non-invasive estimate to cause the non-invasive estimate to conform to the invasive estimate.

7. The apparatus of claim 1, wherein the non-invasive system comprises a system for non-invasively constructing a left-ventricular pressure waveform.

8. A method for validating a non-invasively obtained estimate of LVEDP, the method comprising:
   non-massively obtaining a first estimate of an LVEDP;
   invasively obtaining a second estimate of the LVEDP; and
   comparing the first and second estimates of the LVEDP;
   wherein non-invasively obtaining a first estimate of an LVEDP includes:
   non-invasively obtaining a first pressure waveform;
   non-invasively obtaining a second pressure waveform;
   detecting a time of occurrence of an event in a cardiac cycle; and
   selecting a segment from each of the first and second pressure waveforms and connecting the segments on the basis of the time of occurrence of the event.

9. The method of claim 8, wherein invasively obtaining a second estimate comprises positioning a pulmonary catheter to measure a PCWP.

10. The method of claim 9, generating the second estimate on the basis of the measured PCWP.

11. The method of claim 8, further comprising:
    generating calibration data on the basis of the first and second estimates, and
    applying the calibration data to the first estimate to cause the first estimate to conform to the second estimate.

12. The method of claim 8, wherein obtaining the first estimate comprises non-massively constructing a left-ventricular pressure waveform.

13. A hybrid LVEDP monitor for validating a non-invasively obtained estimate of LVEDP, the monitor comprising:
    means for non-invasively obtaining a first estimate of the LVEDP;
    means for invasively obtaining a second estimate of the LVEDP concurrent with the first estimate; and
    means for validating the first estimate at least in part on the basis of the second estimate;
    wherein means for non-invasively obtaining a first estimate of the LVEDP includes:
    means for non-invasively obtaining a first pressure waveform;
    means for non-invasively obtaining a second pressure waveform;
    means for detecting a time of occurrence of an event in a cardiac cycle; and
    means for selecting a segment from each of the first and second pressure waveforms and connecting the segments on the basis of the time of occurrence of the event.

14. The apparatus of claim 13, wherein the means for invasively obtaining a second estimate comprises a pulmonary catheter having a pressure sensor mounted at a distal tip thereof.

15. The apparatus of claim 13, wherein the means for invasively obtaining a second estimate comprises means for measuring PCWP.

16. The apparatus of claim 13, further comprising means for generating calibration data to be applied to the first estimate to cause the first estimate to conform to the second estimate.

17. The apparatus of claim 13, wherein the means for non-invasively obtaining a first estimate comprises means for non-invasively constructing a left-ventricular pressure waveform.

18. A computer-readable medium having encoded thereon software for validating a non-invasively obtained estimate of LVEDP, said software comprising instructions for causing a processing system to:
    receive data representative of a non-invasively obtained first estimate of an LVEDP; and
    receive data representative of an invasively obtained second estimate of the LVEDP; and
    compare the first and second estimates of the LVEDP;
    wherein the instructions for causing a computer to receive data representative of a non-invasively obtained first estimate of an LVEDP include instructions for causing a computer to:
    receive data representative of a non-invasively obtained first pressure waveform;
    receive data representative of a non-invasively obtained second pressure waveform;
    detect a time of occurrence of an event in a cardiac cycle; and to
    select a segment from each of the first and second pressure waveforms and to connect the segments on the basis of the time of occurrence of the event.

* * * * *

UNITED STATES PATENT AND TRADEMARK OFFICE
CERTIFICATE OF CORRECTION

PATENT NO. : 7,404,800 B2  Page 1 of 1
APPLICATION NO. : 11/105306
DATED : July 29, 2008
INVENTOR(S) : Kevin M. McIntyre It is certified that error appears in the above-identified patent and that said Letters Patent is hereby corrected as shown below:

Please replace claim 8, beginning at col. 9, line 48, with the following corrected version:

8. A method for validating a non-invasively obtained estimate of LVEDP, the method comprising:

~~non-massively~~ non-invasively obtaining a first estimate of an LVEDP;

invasively obtaining a second estimate of the LVEDP; and comparing the first and second estimates of the LVEDP;

wherein non-invasively obtaining a first estimate of an LVEDP includes:

non-invasively obtaining a first pressure waveform;

non-invasively obtaining a second pressure waveform;

detecting a time of occurrence of an event in a cardiac cycle; and selecting a segment from each of the first and second pressure waveforms and connecting the segments on the basis of the time of occurrence of the event.

Signed and Sealed this

Thirty-first Day of March, 2009

JOHN DOLL
*Acting Director of the United States Patent and Trademark Office*